(12) United States Patent
Williams et al.

(10) Patent No.: US 6,818,113 B2
(45) Date of Patent: Nov. 16, 2004

(54) MICROFLUIDIC DEVICE WITH SAMPLE INJECTOR AND METHOD OF USING

(75) Inventors: Stephen J. Williams, San Mateo, CA (US); Hong Dong Tan, San Jose, CA (US); Hung Pin Kao, Fremont, CA (US); Wyatt N. Vreeland, Chicago, IL (US)

(73) Assignee: Aclara Biosciences, Inc., Mountain View, CA (US)

( * ) Notice: Subject to any disclaimer, the term of this patent is extended or adjusted under 35 U.S.C. 154(b) by 10 days.

(21) Appl. No.: 09/780,638

(22) Filed: Feb. 10, 2001

(65) Prior Publication Data

US 2002/0008029 A1 Jan. 24, 2002

Related U.S. Application Data

(60) Provisional application No. 60/185,035, filed on Feb. 25, 2000, and provisional application No. 60/182,049, filed on Feb. 11, 2000.

(51) Int. Cl.[7] .................. B01D 57/02; C02F 1/469; C07K 1/26; C08F 2/58; C25B 15/00
(52) U.S. Cl. .................. 204/453; 204/601; 204/450
(58) Field of Search .................. 204/453, 601, 204/450

(56) References Cited

U.S. PATENT DOCUMENTS

| | | | |
|---|---|---|---|
| 5,599,432 A | | 2/1997 | Manz et al. |
| 5,800,690 A | | 9/1998 | Chow et al. |
| 5,858,187 A | * | 1/1999 | Ramsey et al. ............. 204/451 |
| 5,858,195 A | | 1/1999 | Ramsey |
| 5,869,004 A | | 2/1999 | Parce et al. |
| 5,965,001 A | | 10/1999 | Chow et al. |
| 6,143,401 A | * | 11/2000 | Fischer et al. ............. 174/255 |
| 6,147,675 A | * | 11/2000 | Liu ............................. 345/156 |
| 6,368,871 B1 | | 4/2002 | Christel et al. |
| 6,413,782 B1 | * | 7/2002 | Parce et al. ................. 204/451 |
| 6,428,666 B1 | * | 8/2002 | Singh et al. ................ 204/450 |
| 6,429,025 B1 | * | 8/2002 | Parce et al. ................. 204/400 |
| 6,475,441 B1 | | 11/2002 | Parce et al. |

FOREIGN PATENT DOCUMENTS

| | | |
|---|---|---|
| WO | WO 98/49548 | 11/1998 |
| WO | WO 98/54568 A1 | 12/1998 |
| WO | WO 99/10735 A1 | 3/1999 |

OTHER PUBLICATIONS

US PGPUB 2002/007923 A–Williams, Steven J.; Tan, Hong Dong; Kao, Hung Pin; Vreeland, Wyatt.*
International Search Report for PCT Application No. PCT/US01/04412.
Pier Giorgio Righetti (ED): "Capillary Electrophoresis in Analytical Biotechnology", CRC Press, New York XP008002033, pp. 84–87, 1996.

(List continued on next page.)

Primary Examiner—Mark L. Bell
Assistant Examiner—Jennine Brown
(74) Attorney, Agent, or Firm—Peter J. Dehlinger; Leeann Gorthey; Perkins Coie LLP

(57) ABSTRACT

A method and device for injecting a liquid sample into an electrolyte channel in a microfluidics device is disclosed. The device has a channel network that includes an electrolyte channel having upstream and downstream channel portions and first, second, and third side channels that intersect the electrolyte channel between the two channel portions at first, second, and third ports, respectively. In the method, a sample is moved electrokinetically into the electrolyte channel, to form a defined sample volume therein. By simultaneously controlling the voltage applied to the three side channels, and at least one of the upstream and downstream channel end portions, the sample volume element can be shaped to have a desired leading- and trailing-edge shape and/or distribution of sample components within the volume elements.

19 Claims, 5 Drawing Sheets

OTHER PUBLICATIONS

Jacobson, Stephen C. et al., "Effects of Injection Schemes and Column Geometry on the Performance of Microchip Electrophoresis Devices", *Anal. Chem.* 66, pp. 1107–1113, 1994.

Quirino, Joselito P. et al., "Sample stacking of cationic and anionic analytes in capillary electrophoresis", *Journal of Chromatography A*, 902, pp. 119–135, 2000.

Gebauer, Petr et al., "Sample self-stacking in zone electrophoresis. Theoretical description of the zone electrophoretic separation of minor compounds in the presence of bulk amounts of a sample component with high mobility and like charge", *Journal of Chromatography, 608*, pp. 47–57, 1992.

Guzman, Norberto A. et al., "New Directions for Concentration Sensitivity Enhancement in CE and Microchip-Technology", *LCGC*, vol. 19, No. 1, Jan. 2001.

Yang, Hua et al., "Sample stacking in laboratory-on-a-chip devices", *Journal of Chromatography A*, 924, pp. 155–163, 2001.

Copy of PCT International Search Report from PCT/US02/26393.

Foret, Frantisek et al., "On-column transient and coupled column isotachophoretic preconcentration of protein samples in capillary zone electrophoresis", *Journal of Chromatography*, 608:3–12, 1992.

Reinhoud, N.J. et al., "Capillary isotachophoretic analyte focusing for capillary electrophoresis with mass spectrometric detection using electrospray ionization", *Journal of Chromatography*, 627:263–271, 1992.

Krivankova, Ludmila et al., "Synergism of capillary isotachophoresis and capillary zone electrophoresis", *Journal of Chromatography B*, 689:13–34, 1997.

Waterval, Joop C.M. et al., "Development and validation of transient isotachophoretic capillary zone electrophoresis for determination of peptides", *Electrophoresis* 19:3171–3177, 1998.

Dankova, Mariana et al., "Capillary zone electrophoresis separations of enantiomers present in complex ionic matrices with on-line isotachophoretic sample pretreatment", *Journal of Chromatography A*, 838:31–43, Apr. 9, 1999.

Masar, Marian et al., "Determination of organic acids and inorganic anions in wine by isotachophoresis on a planar chip", *Journal of Chromatography A*, 916:167–174, 2001.

Chen, Shujun et al., "Automated Instrumentation for Comprehensive Isotachophoresis—Capillary Zone Electrophoresis", *Anal. Chem.* 72:816–820, 2000.

Jacobson and Ramsey, "Microchip electrophoresis with sample stacking," *Electrophoresis*, 16: 481–486 (1995).

* cited by examiner

MICROFLUIDIC DEVICE WITH SAMPLE INJECTOR AND METHOD OF USING

This application claims the benefit of U.S. Provisional Patent Application Ser. No. 60/182,049, filed Feb. 11, 2000, and U.S. Provisional Patent Application Ser. No. 60/185,035, filed Feb. 25, 2000. Both applications are incorporated herein by reference.

FIELD OF THE INVENTION

The field of this invention is microfluidic manipulation of fluids and ions.

BACKGROUND

Microfluidics is revolutionizing the way activities are performed in a substantial proportion of chemical and physical operations. One area of microfluidics is the manipulation of small volumes of liquids or liquid compositions on a solid substrate, where a network of channels and reservoirs are present. By employing electric fields with electrically conducting liquids, volumes and/or ions can be moved from one site to another, different solutions formed by mixing liquids and/or ions, reactions performed, separations performed, and analyses carried out. In fact, in common parlance, the system has been referred to as "a laboratory on a chip." Various prior art devices of this type include U.S. Pat. Nos. 6,010,608, 6,010,607, 6,001,229, 5,858,195, 5,858,187 and PCT application No. 96/0547 are a family of applications concerned with injection of sample solutions. See also, U.S. Pat. No. 5,599,432, EPA 0620432, and Verheggen et al., J. of Chromatography 452 (1988) 615–622.

In many of the operations, there is an interest in producing a sharply defined volume of ions as a plug, where the boundaries for specified ions or groups of ions are sharp and either linear or only slightly bowed. At the same time, it may be desired to inject a sample having a well-defined volume. Alternatively, it may be desired to prestack the components in a multicomponent sample, e.g., to improve electrophoretic separation of the components of the sample. In still other applications, it is desired to concentrate sample components present in a sample, prior to injecting the sample for analysis, e.g., by electrophoresis separation.

SUMMARY OF THE INVENTION

It is a general objective of the present invention to provide a microfluidics device and system that can be controlled to achieve these various desired sample-injection features. The invention includes, in one aspect, a method of injecting a liquid sample into an electrolyte channel in a microfluidics device having a channel network that includes an electrolyte channel having upstream and downstream channel portions and first, second, and third side channels that intersect the electrolyte channel between the two channel portions at first, second, and third ports, respectively, where at least one of the ports is axially spaced along the electrolyte channel from the other two ports.

The method includes the steps of (a) supplying a sample to the first side channel, (b) applying across the first side channel and at least one of the other two side channels, a voltage potential effective to move sample in the first channel into a volume element of the electrolyte chamber extending between the first and at least one other port which is axially offset from the first port, (c) simultaneously controlling the voltage applied to the three side channels, and, optionally, one or both of the upstream and downstream channel end portions, to create a sample volume element in the electrolyte channel that has a desired leading- and trailing-edge shape and/or distribution of sample components within the volume elements, and (d) simultaneously controlling the voltage applied to the upstream and downstream channel portion, and to at least two of the side channels, to advance the sample element having a desired leading- and trailing-edge shape and/or distribution of sample components in a downstream direction within the electrolyte channel.

For use in injecting a sample containing a plurality of sample components in a volume element having a substantially uniform distribution of the sample components, the first port is axially disposed between the second and third ports, applying step (b) is effective to move sample in the first channel into a volume element of the electrolyte chamber extending between the second and third ports, and controlling step (c) is effective to move an electrolyte solution from the upstream channel portion through the second port and an electrolyte solution from the downstream portion through the third port, thus to sharpen the upstream and downstream boundaries of the sample volume.

The first port may be axially aligned with the second port, or axially spaced from both the second the third ports. The controlling step (d) is effective to move an electrolyte solution in the upstream channel portion successively through the second, first and third ports, to move sample contained in the three side channels away from the electrolyte channel.

In another embodiment, the method is used for injecting a sample containing a plurality of sample components in a volume element, and prestacking the sample components within the volume element according to their electrophoretic mobilities, where the sample contains a plurality of components with different electrophoretic mobilities and one of a leading-edge ion having an electrophoretic mobility greater than that of said sample components or a trailing-edge ion having an electrophoretic mobility less than that of said sample components. In this method, the first port is axially disposed between the second and third ports, applying step (b) is effective to move sample in the first channel into a volume element of the electrolyte chamber extending between the second and third ports, controlling step (c) is effective to move an electrolyte solution from the upstream channel portion through the second port and an electrolyte solution from the downstream portion through the third port, thus to sharpen the upstream and downstream boundaries of the sample volume, where the electrolyte solution in both the upstream and downstream portions includes the other of the leading-edge or trailing-edge ions, and controlling step (d) is initially effective in stacking the sample components in the sample volume in accordance with their electrophoretic mobilities, by isotachophoretic separation.

As above, the first port may be axially aligned with the second port, or axially spaced from both the second the third ports. The controlling step (d) is effective to move an electrolyte solution in the upstream channel portion successively through the second, first and third ports, to move sample contained in the three side channels away from the electrolyte channel.

Alternatively, for prestacking the sample components, the second port is axially disposed between the first and third ports, applying step (b) is effective to move sample in the first channel into a volume element of the electrolyte chamber extending between the first and second ports, controlling step (c) is effective to move a solution containing one of a leading-edge ion having an electrophoretic mobility greater than that of said sample components or a trailing-edge (terminating) ion having an electrophoretic mobility less than that of said sample components from the third channel into the second channel, and controlling step (d) is initially effective in stacking the sample components in the sample volume in accordance with their electrophoretic mobilities, by isotachophoretic separation. The other of the leading- or trailing-edge ion is contained in the upstream and downstream portions of the electrolyte channel.

In another embodiment for injecting a sample containing one or more sample components, and concentrating the component(s) at the upstream or downstream side of the sample volume, the first, second, and third ports are axially spaced from one another, and the second port is disposed between the first and third ports. Applying step (b) includes applying a DC voltage potential across the first and second side channels, to move sample in the first channel into a volume element of the electrolyte chamber extending between the first and second ports, and controlling step (c) includes applying an AC voltage between the third side channel and an upstream or downstream channel portion, where the first and second ports are disposed between and spaced from the third side channel and channel portion to which the AC voltage is applied, thereby to concentrate sample components in the sample volume at an end of the sample volume adjacent the channel portion to which the AC voltage is applied.

In still another embodiment for concentrating sample components, the first and third channels are axially aligned or nearly so on opposite sides of the electrolyte channel, the second channel is axially spaced from the first and third channels, applying step (b) includes applying a DC voltage potential across the first and second side channels, to move sample in the first channel into a volume element of the electrolyte chamber extending between the first and second ports, and controlling step (c) includes applying an AC voltage between the third channel and the adjacent upstream or downstream channel end portion between the third side channel and an upstream or downstream channel portion, thereby to concentrate sample components in the sample volume at an end of the sample volume adjacent the channel portion to which the AC voltage is applied.

Forming another aspect of the invention is a microfluidic system designed for use in injecting a defined-volume liquid sample into a capillary electrolyte channel, for transport through the channel. The device includes (a) a microfluidic device having a channel network that includes such an electrolyte channel having upstream and downstream channel portions and first, second, and third side channels that intersect the electrolyte channel between the two channel portions at first, second, and third ports, respectively, where at least one of the ports is axially spaced along the electrolyte channel from the other two ports, (b) ports for supplying liquid medium to the electrolyte channel and the side channels, and (c) upstream and downstream electrodes, and first, second, and third electrodes adapted to communicate with liquid medium contained in upstream and downstream portions of the electrolyte channel, and the first, second, and third side channels, respectively, and A voltage controller (d) operatively connected to the upstream downstream, and first, second, and third electrodes, for: (i) applying across the first side channel and at least one of the other two side channels, a voltage potential effective to move a liquid sample contained in the first channel into a volume element of the electrolyte chamber extending between the first and at least one other port which is axially offset from the first port, (ii) simultaneously controlling the voltage applied to the three side channels, and at least one of said upstream and downstream channel end portions, to create a sample volume element in the electrolyte channel that has a desired leading and trailing-edge shape and/or distribution of sample components within the volume elements, and (iii) simultaneously controlling the voltage applied to the upstream and downstream channel portion, and to at least two of the side channels, to advance the sample element having a desired leading- and trailing-edge shape and/or distribution of sample components in a downstream direction within the electrolyte channel.

The device has the structural and controlled-voltage features described above.

These and other objects of the invention will become more fully apparent when the following detailed description of the invention is read in conjunction with the accompanying drawings.

DETAILED DESCRIPTION OF THE INVENTION

I. Microfluidic System

The invention includes, in one aspect, a microfluidic system for use in injecting a defined-volume liquid sample into a capillary electrolyte channel, for transport through the channel. By "defined volume" is meant that the volume injected has a known volume defined by volume of the electrolyte channel in which the sample is loaded, as will be seen below. The transport through the electrolyte channel may be for purposes of carrying the sample to another station in the system, for separation of sample components, e.g., by electrophoretic separation along the electrolyte channel, or for analysis of components at one or more positions along the length of the channel, e.g., at a specified reaction site within the channel.

Figure 1:
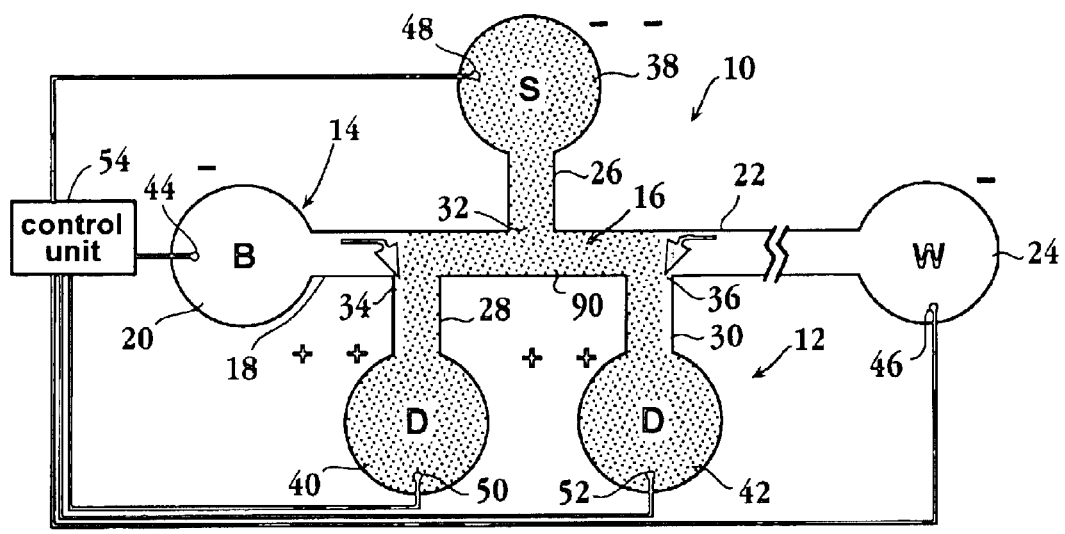
FIG. 1 shows a sample loading step in a microfluidic system having a side-channel configuration in accordance with one embodiment of the invention.

One exemplary system in accordance with the invention is shown at 10 in FIG. 1. The system includes a microfluidics device, shown generally at 12 containing a channel network 14. As will be described below, the channel network may be formed conventionally in a microfluidic substrate, such as a silicon or polymer substrate having a network of capillary channels formed in an upper surface of the substrate, and enclosed by a lid attached to the upper substrate surface. The channel network includes an electrolyte channel 16 having an upstream portion 18 that communicates with a buffer or electrolyte reservoir 20, and a downstream portion 22 that communicates with a waste reservoir 24. In operation, and as will be described below, sample is injected into the electrolyte channel between the upstream and downstream channel portions, and subsequently moved in a downstream direction (toward the right in the figure) in the electrolyte channel for sample separation, analysis, and/or transport to another site in the device.

Also included in the channel network are first, second, and third side channels 26, 28, 30, respectively which intersect the electrolyte channels at ports 32, 34, and 36, respectively. The three ports are disposed between the upstream and downstream electrolyte channel portions, and are axially spaced from one another, as shown in the embodiments in FIGS. 1 and 2, although in some applications, two of the side channel ports may be axially aligned on different sides of the electrolyte channel, as will be discussed with reference to FIG. 3. The designation of particular side channels as "first", "second", and "third" channels is arbitrary and may vary among the various methods described below. More generally, the "first" channel will be used to designate the channel through which sample material is supplied, and the "second" and "third" channels will designate either drain channels into which the sample is received, or channels from which other components may be supplied to the electrolyte channel.

Channels 26, 28, and 30, communicate at their distal ends with sample reservoir 38, and drain reservoirs 40, 42, respectively, as shown. At least one, and preferably all of the reservoirs have ports (not shown) at which liquid material can be added to the reservoirs. Each reservoirs provides, or is adapted to receive, an electrode, such as electrodes 44, 46, 48, 50, and 52 in reservoirs 20, 24, 38, 40, and 42, respectively. The electrodes may be formed on the substrate or formed independently, e.g., on an electrode plate for placement on the substrate for electrode contact with liquid in the associated reservoirs. Each electrode, in turn, is operatively connected to a control unit or voltage controller 54, which operates in various modes described below, to produce one of a selected type of desired sample-injection modes.

The relative spacing between and among the three side channels, and the cross-sectional area of the electrolyte channel in the region of channel injection will determine the desired volume for sample plug to be injected. Obviously, for a given volume, the larger the cross-sectional area of the channel, the smaller may be the spacing. The spacing may be symmetrical or asymmetrical, depending upon the particular configuration, usually being at least about 10% of the total length of the plug away from the source channel, as measured center-to-center of the drain channels. The spacing from channel center to channel center will be in the range of about 1 $\mu$m to 3 cm, more usually about 5 $\mu$m to 1 mm. Volumes for the plug will generally be in the range of about 1 nl to 1 $\mu$l, more usually in the range of about 1 nl to 10 nl, although larger or smaller volumes may find application in particular situations.

Figure 2:
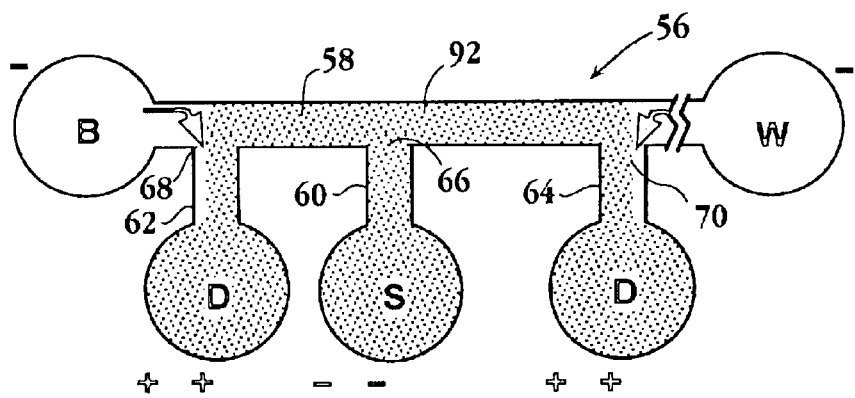
FIG. 2 shows a sample loading step corresponding to FIG. 1, in a second side-channel configuration, in accordance with the invention.
Figure 3:
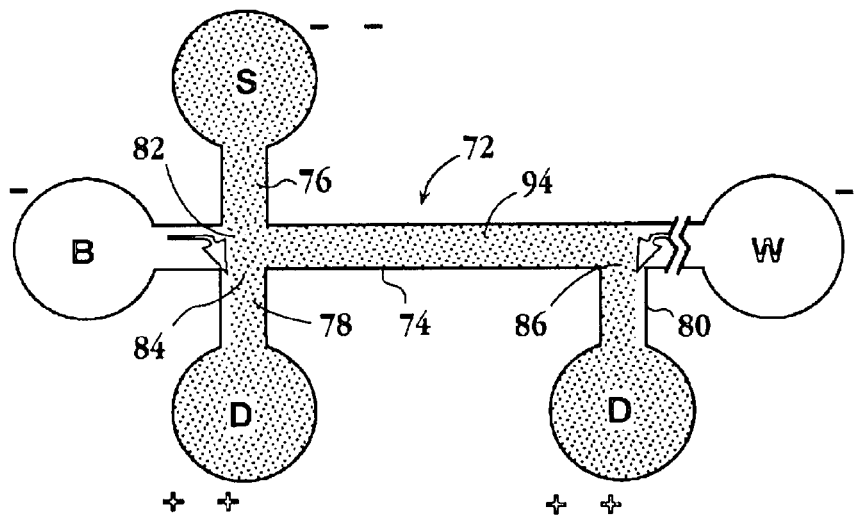
FIG. 3 shows a sample loading step corresponding to FIG. 1A, in a third side-channel configuration, in accordance with the invention.

Three alternative configurations of side channels are illustrated in FIGS. 1–3. In the FIG. 1 configuration, the first side channel port is disposed between and axially spaced from the second- and third-channel ports, and on opposite sides of the electrolyte channel (recognizing that that the "first" channel from which sample is injected may be any of the three channels, depending on the particular sample-injection configuration selected). In the embodiment shown in FIG. 2, a channel network 56 includes an electrolyte channel 58 and first, second, and third side channels 60, 62, and 64, respectively, which intersect channel 58 at three ports 66, 68, and 70, respectively, that are axially spaced from one another and disposed on the same side of the electrolyte channel.

FIG. 3 shows an embodiment having a channel network 72 that includes an electrolyte channel 74 and first, second, and third side channels 76, 78, 80, respectively, that intersect channel 74 at three ports 82, 84, 86, respectively, where the first and second side channels are axially aligned, and have ports on opposite sides of the electrolyte channel, and both are axially spaced from the third channel.

Considering now the fabrication of the microfluidics device in the system, the substrate or card in which the channels are present will generally have a thickness of at least about 20 $\mu$m, more usually at least about 40 $\mu$m, and not more than about 0.5 cm, usually not more than about 0.25 cm. The width of the substrate will be determined by the number of units to be accommodated and may be as small as about 2 mm and up to about 6 cm or more. The dimension in the other direction will generally be at least about 0.5 cm and not more than about 50 cm, usually not more than about 20 cm. The substrate may be a flexible film or relatively inflexible solid, where the microstructures, such as reservoirs and channels, may be provided by embossing, molding, machining, etc. The channel dimensions will generally be in the range of about 0.1 $\mu$m to 1 mm deep and about 0.5 $\mu$m to 1 mm wide, where the cross-section will generally be 0.1 $\mu$m$^2$ to about 1 mm$^2$. The channel lengths will vary widely depending on the operation for which the channel is to be used, generally being in the range of about 0.05 mm to 50 cm, more usually in the range of about 0.5 mm to 20 cm. The main and side channels may have the same or different cross-sectional areas, as well as the same or different shapes.

Depending on the flow pattern desired in the junction region, the side channels may be of larger or smaller cross-section than the main channel. The reservoirs will generally have volumes in the range of about 10 nl to 100 $\mu$l; more usually have volumes in the range of about 500 nl to 10 $\mu$l. The reservoirs may be cylindrically shaped, conically shaped, e.g. the frustum, or other regular shape.

The fabrication of the device may include the substrate comprising the microfeatures, a supporting film, an enclosing film, or combinations thereof. A supporting film will generally be at least about 40 $\mu$m and not more than about 5 mm thick. The film used to enclose the channels and the bottom of the reservoirs will generally have a thickness in the range of about 10 $\mu$m to 2 mm, more usually in the range of about 20 $\mu$m to 1 mm. The selected thickness may be controlled by the desire for good heat transfer, e.g. temperature control, but otherwise will usually be one of convenience and assurance of good sealing and the manner in which the devices will be used to accommodate instrumentation. The enclosing film, where the bottom of the substrate is totally closed, will also have a thickness coming within the above range, and will include perforations in register with the reservoirs or other feature requiring access, while enclosing the channels. Therefore, the ranges are not critical.

As indicated, the substrate may be a flexible film or inflexible solid, so the method of fabrication will vary with the nature of the substrate. For embossing, at least two films will be used, where the films may be drawn from rolls, one film embossed and the other film adhered to the embossed film to provide a physical support. The individual units may be scored, so as to be capable of being used separately, or the roll of devices retained intact. See, for example, application Ser. No. PCT/98/21869. Where the devices are fabricated individually, they will usually be molded, using conventional molding techniques. The substrates and accompanying film will generally be plastic, particularly organic polymers, where the polymers include addition polymers, such as acrylates, methacrylates, polyolefins, polystyrene, etc. or condensation polymers, such as polyethers, polyesters, polyamides, polyimides, dialkyl siloxanes, etc., although glasses, silicon or other material may be employed. Desirably, the polymers will have low fluorescence inherently or can be made so by additives or bleaching, e.g. photobleaching. A film will usually be placed over the substrate to at least enclose the channels, which film will usually have openings for communicating with the reservoirs and, where appropriate, introducing electrodes into the reservoirs. The enclosing film will be adhered to a substrate by any convenient means, such as thermal bonding, adhesives, etc. The literature has many examples of adhering such films, see, for example, U.S. Pat. Nos. 4,558,333; and 5,500,071.

II. Sample-injection Method

The system described above is designed to carry out the various sample-injection operations detailed in subsections A–C below. Generally, the sample-injection method of the invention includes first supplying a sample to the first side channel. The sample is typically an aqueous sample containing multiple biological or biologically active components, such as different-length and sequence DNA fragments, different proteins, or therapeutic compounds or the like, or fluorescent reporter molecules, which are to be transported through, analyzed in, and separated along the electrolyte channel, after injection into the channel. In one exemplary application, the sample contains a plurality of compounds, such as nucleic acids compounds, having different electrophoretic mobilities, and the downstream portion of the electrolyte channel contains an electrophoretic medium, for zone or capillary electrophoresis (CE) separation of the components in the electrolyte channel.

In addition, liquid is added to the other channels in the device, preferably through a port communicating with an associated reservoir in the device. In general, the remaining channels and reservoirs are filled with an electrolyte solution, e.g., a standard electrophoresis solution containing between about 2–250 mM buffering salts.

With the device so loaded, the control unit is operated to place a voltage across the first side channel and at least one of the other two side channels, and in particular, one that is axially spaced from the first side channel. The voltage and polarity of the voltage potential is such as to move sample material electrokinetically from the sample reservoir through the sample channel, into and through the segment of electrolyte channel between the voltage controlled side channels, and into the second, and optionally third side channel, and reservoirs. The electrokinetic movement may be bulk-phase electroosmotic flow (EOF), electrophoretic movement of individual components in the sample, or a combination of both. The portion of the electrolyte channel between the ports of the voltage-controlled side channels thus becomes filled with a sample volume which is defined by the volume of the channel between, and at least partially including, such ports. Typically, the voltage applied across the side channels is a DC voltage of between about 10–5,000 volts.

According to an important feature of the invention, a desired shape of the leading and trailing edges of the sample volume, and/or a desired distribution of sample components within sample volume is achieved by simultaneously controlling the voltage applied to the three side channels and, optionally, at least one of the upstream or downstream electrolyte channel portions. Subsections A and B below detail a sample-loading method in which the leading and trailing edges of the sample volume are shaped by inward flow of buffer or buffer ions from the two channel portions into the second and third side channels; subsection C, a sample loading method in which sample components are concentrated at one end of the sample volume by dielectric focusing. The two steps, in which sample is loaded from the first channel into the electrolyte channel, and then shaped and or concentrated are also referred to herein as a sample-loading step.

After sample loading, and appropriate shaping and/or distributing of sample components in the sample volume, the control device is operated to simultaneously control the voltage applied across the upstream and downstream channel portions, and at least two of the side channels, to advance the sample in a downstream direction in the electrolyte channel. This step is also referred to herein as a sample-injection step. In the method described in subsection A and C, the sample injection involves moving the sample volume as a shaped sample plug (subsection A) or a plug with concentrated components (C) into the downstream portion of the electrolyte channel; in subsection B, the sample injection initially acts to prestack different sample components in the sample by isotachophoresis, then move the sample components by electrophoretic movement. The three sample-injection modes will now be considered in greater detail.

A. Defined-volume Sample Injection

FIGS. 1–3 illustrate the sample-loading step in three different side-channel configurations, for producing a defined-volume sample plug with shaped leading and trailing edges. In the FIG. 1 embodiment, the control unit operates to apply a DC voltage potential across the first side channel and each of the second and third side channels, to move sample material from sample reservoir 38 into and through the electrolyte channel between ports 34, 36, and into the second and third side channels as shown. The polarity of voltage potential, indicated arbitrarily as V(−) to V(+), is selected to move sample electrokinetically in the desired direction. Typically, the voltage potential gradient across the side arms is between about 10 and 500 V/cm.

At the same time, as part of the sample-loading step, a voltage potential is applied to the upstream and downstream portions of the electrolyte channel, to move buffer or buffer ions in reservoirs 20, 24 toward and into side channels 28, 30. That is, voltage control at all five reservoirs is controlled simultaneously. As indicated, the voltage difference across each end portion of the channel and the associated side channel is less than that across the same side channel and first side channel, so that buffer flow from the opposite ends of the electrolyte channel is confined to the two outer side channels, as indicated.

By controlling the field strengths at the junction area, the proportion of the cross-sectional area of the two streams (sample and electrolyte buffer) in the drain channels may be varied from about 5:95 to 95:5 for the sample and buffer streams, more usually 10:90 to 90:10 and preferably about 25:75 to 75:25. Too small a proportion of the buffer stream or sample stream will diminish the linearity and sharpness of the edge of the plug. For the flow of positive ions, generally, there will be is a lower potential between the source and the drain. The relative field strengths will be a function of the voltage at the electrode, the distance of the electrode from the junction area, the electrical resistance of the streams, and the like. Therefore, setting forth voltages is not meaningful without knowledge of the other parameters. Nevertheless, for a conventional system with distances of the electrodes from the junction area in the range of about 1 to 20 mm, and cross-sectional areas in the range of about $1\times10^{-4}$ to $4\times10^{-2}$ mm$^2$, with the common salt concentrations used for microfluidic devices, field strengths at the junction area for the source channel, the drain channels, the main channel and the sample plug in the main channel would be in the range of ratios of 1 to 0.5: 100 to 0.01: 100 to 0.01:100.

The sample-loading voltages are preferably applied for a period of time needed to obtain a representative sample composition in the sample volume. In particular, where sample movement involves a component of electrophoretic sample movement, the voltage is applied for a period needed to move the slowest moving component of the sample into and through the sample volume, as described, for example, in EPO 0,620,432 A1. As seen in FIG. 1, the sample-loading steps are effective to move a defined-volume sample plug 90 into the electrolyte channel, and confine the leading and trailing edges thereof to well-defined boundaries just inside the respective side-channel ports.

FIG. 2 illustrates the same sample-loading steps in a similar side-channel configuration, but where the first (sample) channel is disposed on the same side of the electrolyte channel. The operation and sample-loading results are substantially identical to that described in FIG. 1 producing a defined-volume sample plug 92 with shaped leading and trailing edges.

In the FIG. 3 configuration, the first and second channel ports are axially aligned, so that the sample volume is defined as the region of the electrolyte channel between the aligned first and second ports, and the third downstream port. The sample-loading steps are the same as those described with respect to FIG. 1, producing a defined volume sample plug 94 with shaped leading and trailing edges.

Figure 4A:
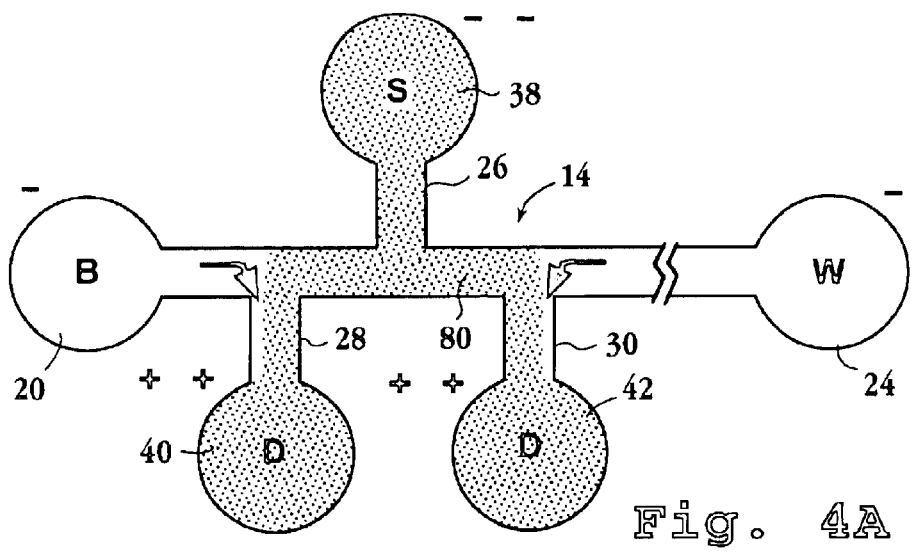
FIGS. 4A–4C show steps in loading and injecting a defined-volume sample plug in accordance with one general embodiment of the method of the invention.
Figure 4B:
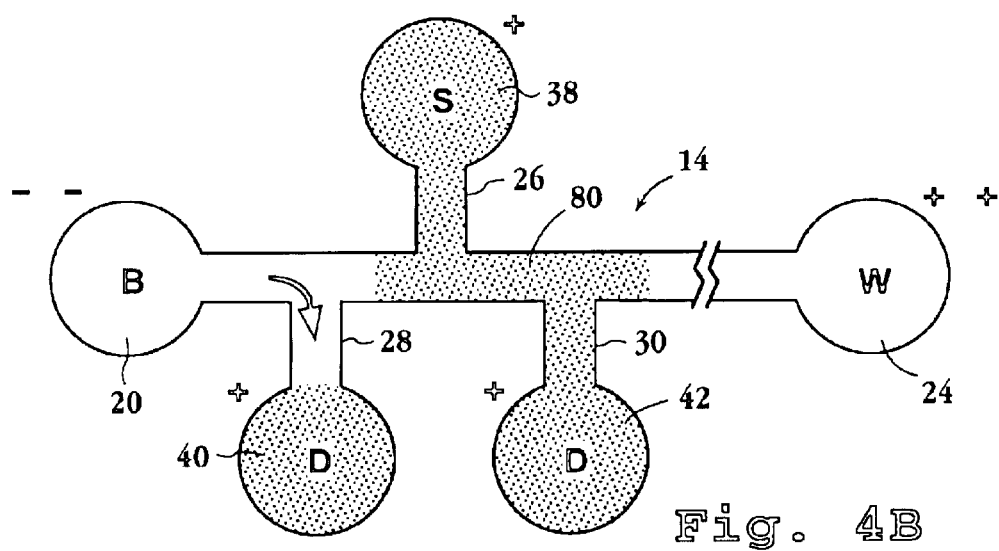
Figure 4C:
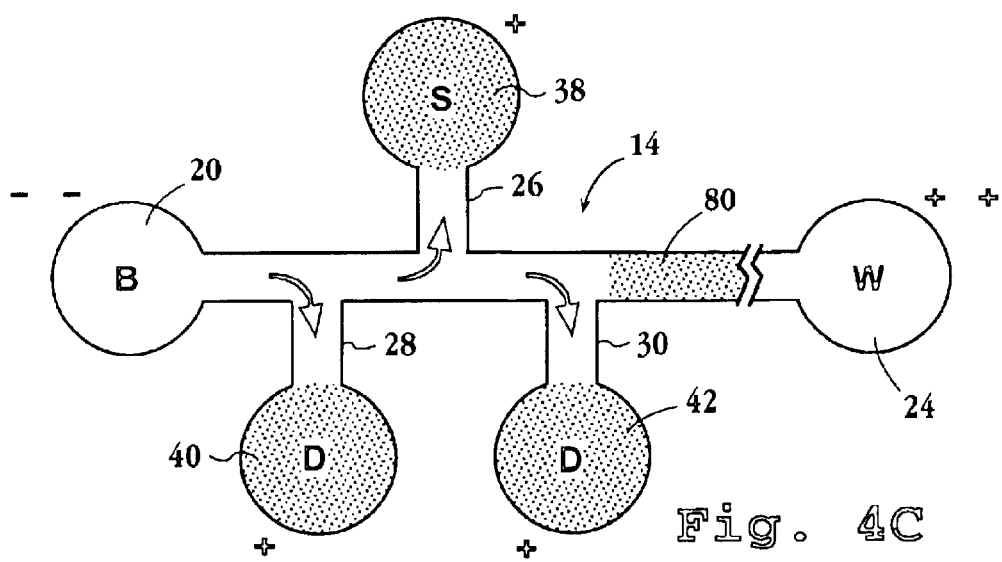

FIGS. 4A–4C illustrate various stages of sample volume movement during the sample-injection step in the device illustrated in FIG. 1, where FIG. 4A shows the condition of the device during sample loading.

To inject defined-volume sample 80 in a downstream direction in the figures, the control unit now operates to apply a "sample-moving" voltage across the upstream and downstream portions of the electrolyte channel, that is, across reservoirs 20, 24, as indicated in FIG. 4B. The voltage potential, expressed as V/cm, and voltage polarity are comparable to those applied across the side channels during sample loading, and are such as to move the sample plug, or the components therein, by EOF and/or electrophoretic movement, in a downstream direction at a desired rate of sample movement.

Simultaneously, a lesser voltage potential is applied to each of the three side channels to direct electrolyte moving from reservoir 20 in a downstream direction also into the three side channels, to move sample in the side channels away from the electrolyte channel. As can be seen in FIGS. 4B and 4C, this "push-back" effect is designed to eliminate unwanted diffusion or migration of sample components into the electrolyte channel upstream of the sample plug during sample injection.

This five-channel configuration, with simultaneous control at each of the five channels during sample loading and sample injection, has important advantages over simple channel-cross or double-T configurations that are known in the prior art. In particular, the system allows for precisely defined sample volumes that are shaped (have sharp interface boundaries) at both upstream and downstream sample volume edges. In this way, precisely known volumes of sample can be metered into the electrolyte channel.

B. Sample Injection with Transient Prestacking

In this method, a sample injected as a defined volume in the electrolyte channel is prestacked during sample injection by transient isotachophoresis (ITP), e.g., to improve electrophoretic separation of the sample in the downstream portion of the electrophoretic channel. The method is illustrated in FIGS. 5A–5C with respect to the side-channel configuration of FIG. 1, it being recognized that other side-channel configurations are suitable for the method, as will be appreciated below.

The theory of ITP separation has been described, e.g., in "Capillary Electrophoresis in Analytical Biotechnology", Righetti, P. G., ed, 1996, CRC Press, pp. 84–87. Briefly, a sample containing components with different electrophoretic mobilities is placed between a buffer with a leading edge ion and one containing a terminating or trailing-edge ion. The leading edge ion is a small ion, such as the chloride ion, having an electrophoretic mobility greater than that of any of the sample components. The counterion of the leading-edge ion is chosen for its ability to buffer the solution. Similarly, the trailing edge ion is one having an electrophoretic mobility lower than the slowest-migrating sample components. With the application of a voltage potential across the sample, sample components will band, by migration through the sample, until the fastest moving sample components are concentrated adjacent the leading-edge buffer and the slowest moving components, against the trailing edge buffer.

Figure 5A:
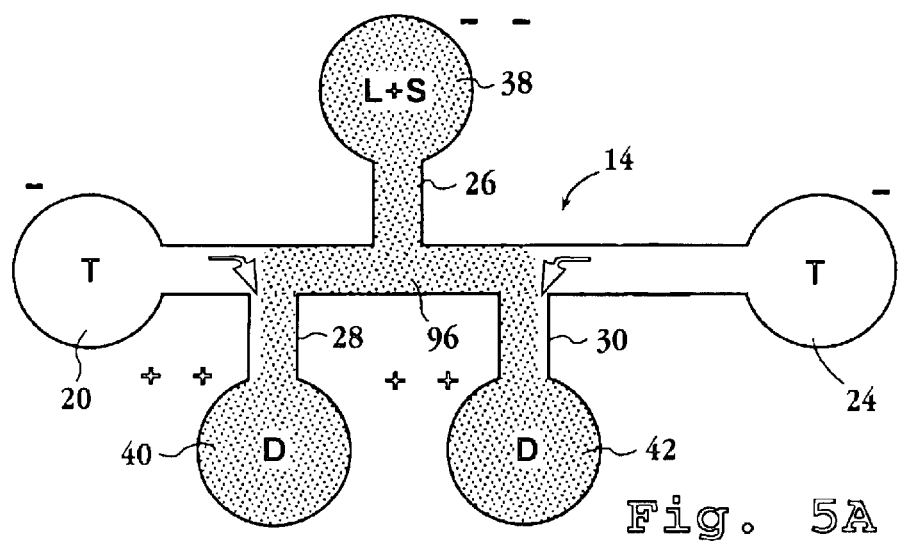
FIGS. 5A–5C show steps in loading and prestacking sample components in accordance with another general embodiment of the method of the invention.
Figure 5B:
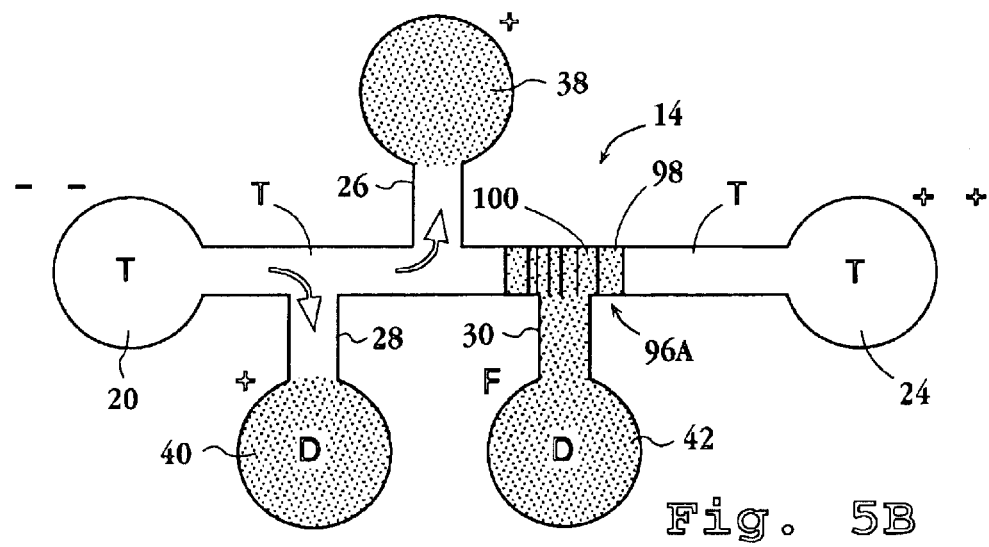
Figure 5C:
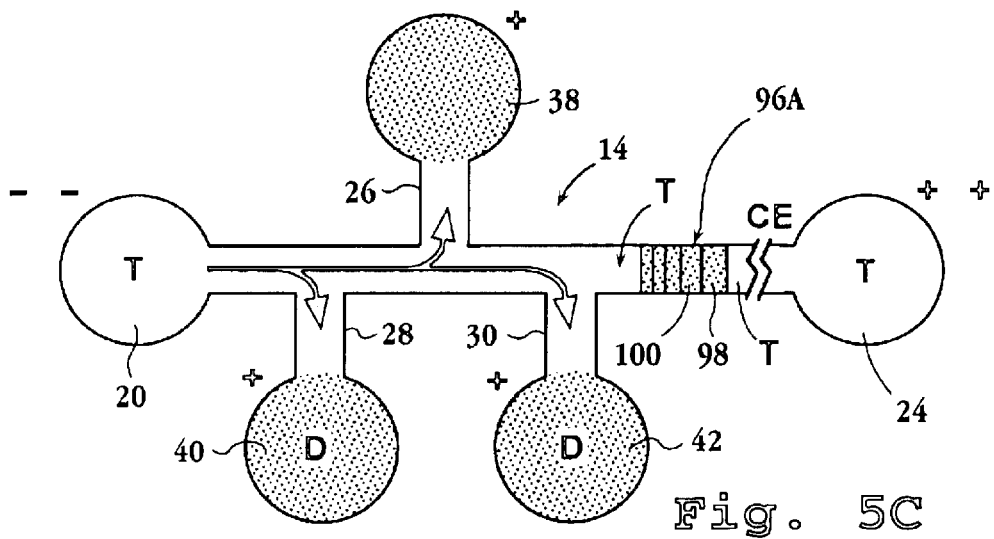

The transient ITP method employed in the method illustrated in FIGS. 5A–5C differs from the above approach in that the sample is formulated to contain either the leading-edge or trailing-edge ion, and it is placed between, that is, injected between a buffer containing the other ion, e.g., the trailing-edge ion when the sample contains the leading-edge ion. With the application of voltage across the sample, the sample components will band as in normal ITP, but at the same time the leading-edge and trailing-edge ions in the sample, and bordering the sample will mix, leading to a loss of the ITP ion-migration gradient needed for ITP. As the ion mixing occurs, the sample components begin to migrate under ordinary electrophoretic forces, and further separation is based on electrophoretic separation, as the sample components move down the electrolyte channel.

In the embodiment shown in FIGS. 5A–5C, the leading-edge ion (L) is included with the sample components (S) and injected, in accordance with the method described with respect to FIG. 1, between an electrolyte containing the trailing ion (T). That is, reservoirs 20 and 24 and the electrolyte channel therebetween is initially filled with a buffer solution containing the trailing ion, and the trailing-ion buffer is directed into the second the third side channels during sample injection, to form sharp edge boundaries of the sample volume, indicated at 96. Optimal injection times will depend on the mobilities of the sample components, the size of the sample, and the volume of the junction area. Usually injection times will be at least 1 sec and not more than about 200 sec, usually not more than about 90 sec, more usually in the range of about 5 to 60 sec.

Since stacking will commence from the trailing ion, the sample components will begin stacking at the upstream end of the sample and proceed in a downstream direction, where the reservoirs buffers contain the trailing ion, and will stack in the reverse direction, from the front of the sample volume in a right-to-left direction when the trailing ion is included in the sample. In both cases, the sample bands will be arrayed so that faster-migrating components are positioned downstream of slower-moving components.

The concentrations of the electrolytes will generally be in the range of about 0.1 to 1,000 mM, more usually in the range of about 1 to 100 mM. For the terminating electrolyte, the range will generally be about 1 to 100 mM, while for the leading electrolyte, the range will generally be from about 1 to 1000 mM. The particular concentration will be affected by the nature of the electrolyte and sample, the conditions under which the ITP is carried out, and the like. The buffer concentration may be readily optimized empirically in a specific system. The sample concentration may also vary widely, depending on the nature of the sample, the number of components, the ease with which they can be separated, etc. Generally, the total concentration of the components of the sample to be assayed will be in the range of about 0.1 pM to 1 $\mu$M.

Illustrative electrolytes (refers primarily to the salts that are used to provide the leading and terminating ions include, sodium chloride, HEPES, TAPS, sodium citrate, sodium phosphate, sodium borate, sodium tetraborate, sodium taurodeoxycholate, CAPS, sodium glycinate, Tris-CI, sodium formate, sodium ethane sulfonate, sodium pentane sulfonate, sodium tartrate, etc. While TRIS and sodium are the most common counterions, they may be replaced with ammonium, lithium, potassium, magnesium, etc., for the cations, and bromide, nitrate, nitrite, sulfate, cyanide, etc. for the anions, as well as by the electrolyte ions indicated above. The ionic strength of the sample as compared to the electrolyte solution in the main channel may vary widely, may be less than, be at least equal to or greater than the ionic strength of the electrolyte solution in the main channel. This can be achieved by the addition of salts, such as alkali metal chlorides to the sample solution, in the range of about 5 to 250 mM, more usually in the range of about 5 to 100 mM, and preferably in the range of about 20 to 75 mM.

After the sample-loading step illustrated in FIG. 5A, the control unit operates to apply a voltage potential across the upstream and downstream portions of the electrolyte channel, as illustrated in FIG. 5B, as part of the sample-injection step. Now the sample components will become stacked in accordance with their mobility as the sample ions move through the sample volume. The sample volume, indicated at 96A, has now been condensed into a series of stacked bands, such as bands 98, 100. For a sample containing leading-edge ions, the transition from ITP to zone electrophoresis occurs when the sample ions begin to overtake trailing ions in the downstream channel portion. In samples containing trailing-edge ions, the transition occurs when the leading edge ions in the upstream channel portion begin to overtake the sample ions. Thus, with continued application of the sample-injection voltage, as illustrated in FIG. 5C, the prestacked components are further separated by electrophoresis, or otherwise further process in the electrolyte channel as individual-component bands.

Figure 6A:
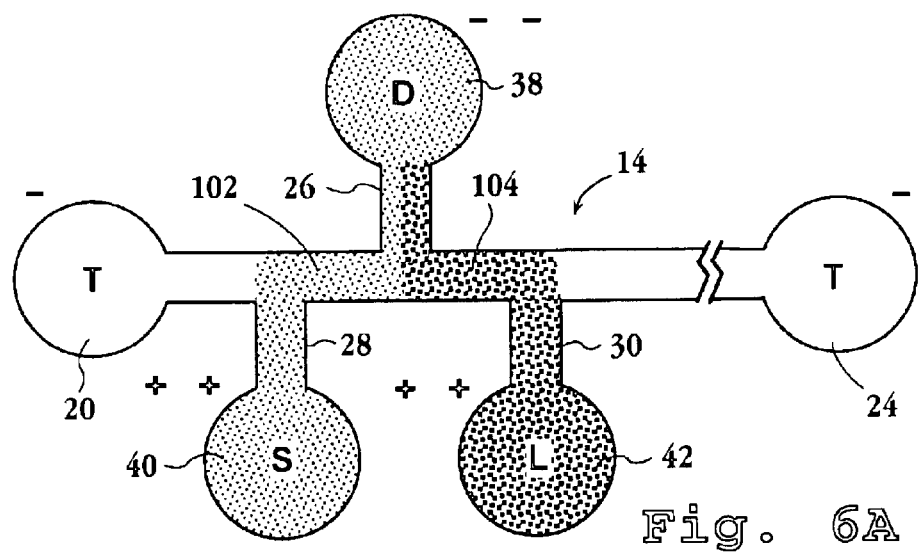
FIGS. 6A–6C show steps in an alternative method for loading and prestacking sample components in accordance with the invention.
Figure 6B:
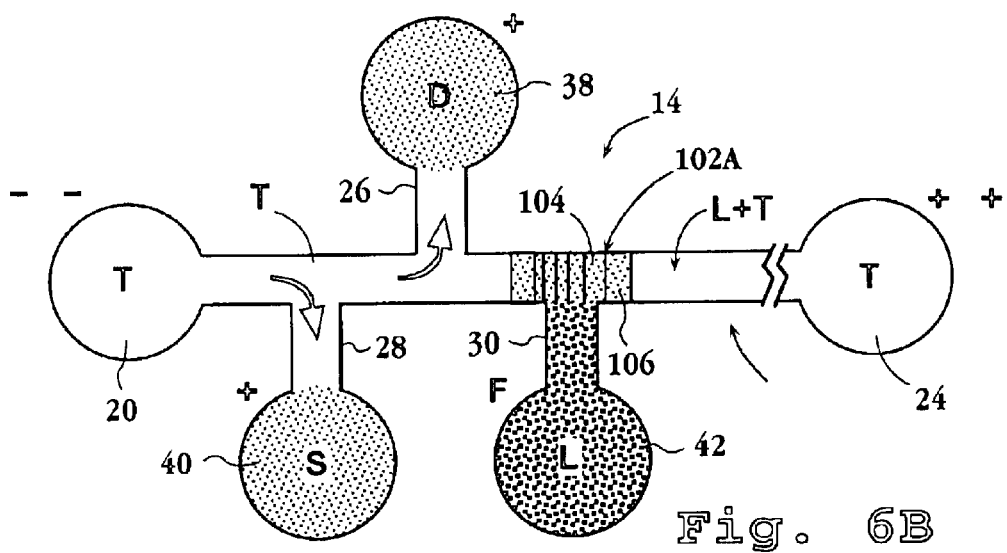
Figure 6C:
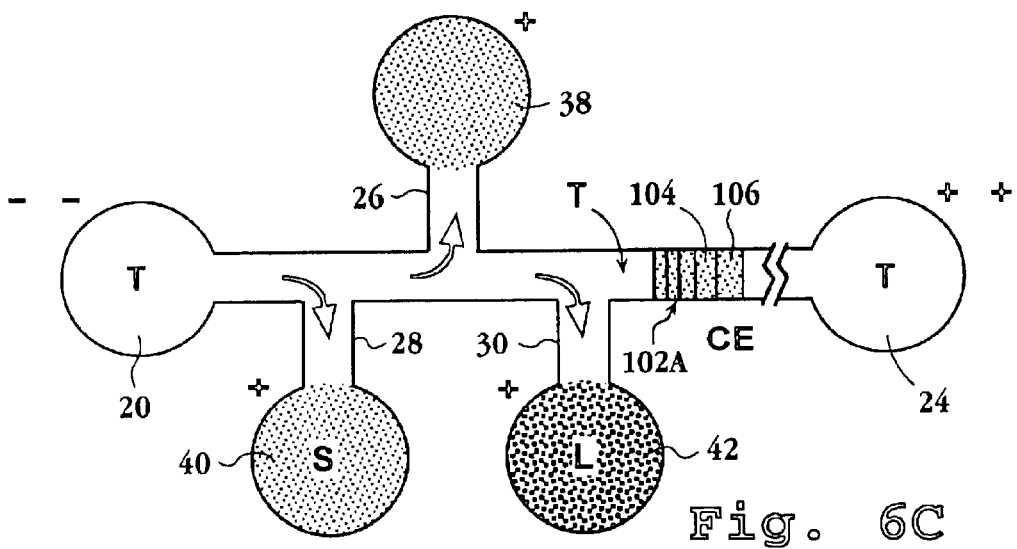

FIGS. 6A–6C illustrate an alternate ITP method of sample injection, in accordance with the invention. In this method, initial sample injection occurs between a first channel 28, and a second intermediate channel 26, by application of a voltage potential across the two channels. At the same, leading ion L is supplied from third channel 30 to second channel 26, by application of a voltage potential with the same polarity. As seen in FIG. 6A, this sample injection produces a sample volume element 102 in the electrolyte channel between the first and second channel ports, and a plug 104 of leading ion immediately downstream of the sample volume, and separated therefrom by a sharp boundary. Thus, proceeding in an upstream-to-downstream direction, the electrolyte channel includes a solution containing the trailing ion supplied from reservoir 20, a sample volume from reservoir 40, a plug of solution containing the leading ion supplied from reservoir 42, and the solution containing the trailing ion. Alternatively, either or both of the sample in reservoir 40 and solution in reservoir 20 may also contain leading ion L.

For sample injection, a voltage potential is applied across reservoirs 20 and 24, as indicated in FIG. 6B. Since the sample volume is confined between plugs of leading and terminating ions, the sample components in the sample volume will initially stack by ITP, as above, forming a sample plug 102A having stacked bands such as bands 104, 106, where the fastest moving bands stack initially against the leading ion. This effect is transient only, because the sample ions, having higher mobilities than the trailing ion T, will eventually overtake these ions and the system transitions from ITP to capillary electrophoresis (CE), where the sample ions are separated by their relative mobilities, as above.

It will be appreciated that the roles of the leading and terminating ions can be reversed in the method just described, where leading ions are supplied from reservoir 20, terminating ions from reservoir 40, sample from reservoir 42, and leading ions from reservoir 24.

The method provides significant advantages over combined ITP/CE methods known in the prior art. First, with respect to the embodiment illustrated in FIGS. 5A–5C, the sample loading step involving control at all five electrodes is effective to create both a well-defined volume element and a sharp boundary between the volume element and the trailing (or leading) ion. Accordingly, the amount of sample material can be precisely metered, and the ITP prestacking can be precisely controlled. Similarly, in the embodiment illustrated in FIGS. 6A–6C, a sample volume of defined volume is injected between solutions of terminating and leading ions, where the sample injection procedure produces a sharp interface between the sample and leading ion, also resulting in metering of a precise amount of sample material and improved control of the ITP.

C. Sample Injection with Dielectrophoretic Sample Concentration

Figure 7A:
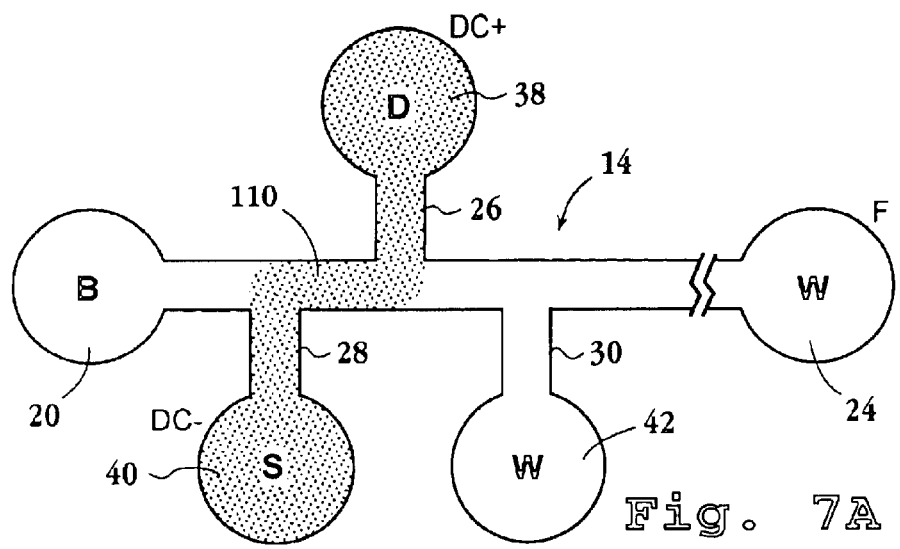
FIGS. 7A–7C show steps in loading, concentrating, and injecting sample components in accordance with a third general embodiment of the method of the invention.
Figure 7B:
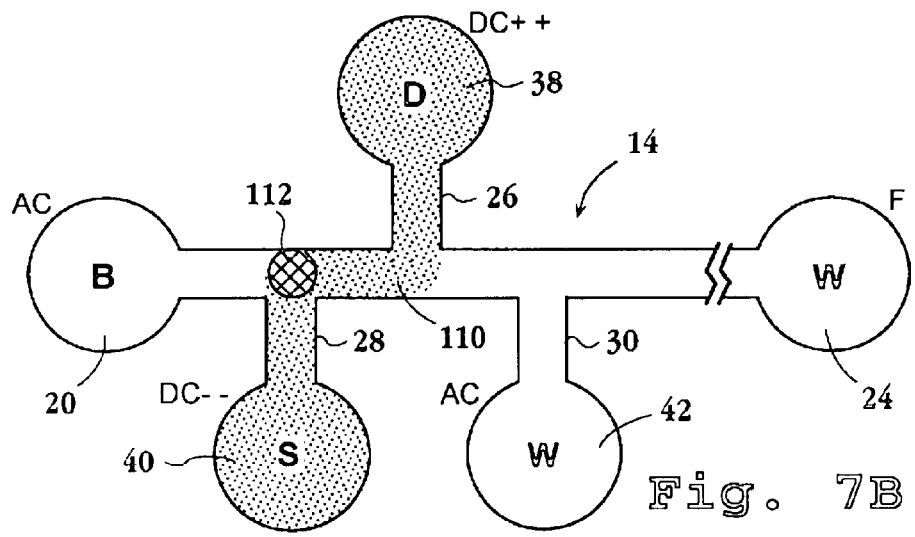
Figure 7C:
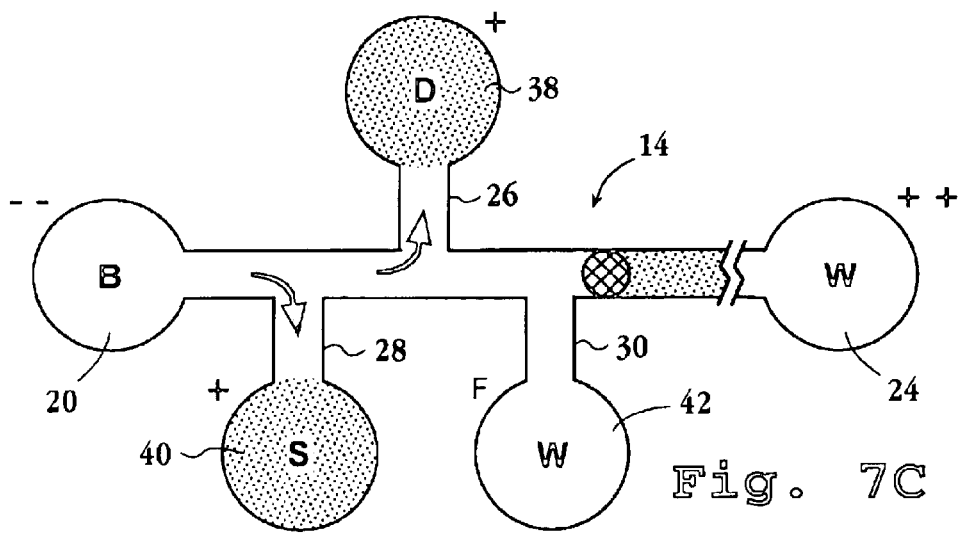

In a third method, the system of the invention is used to concentrate sample components at or adjacent one end of the sample volume in the electrolyte channel. The method is illustrated in FIGS. 7A–7C, which shows a channel network 14 identical to that of FIG. 1. The initial step in sample loading is shown in FIG. 7A. Here sample in first channel 26 is injected into the electrolyte channel and into a second adjacent channel 26, by applying a DC voltage potential across the first and second channels, forming a defined sample volume 100 in the electrolyte channel. The voltage potential and polarity are similar to those given above for sample loading.

At the same time, and as part of the sample-loading step, an AC voltage is applied across the third channel 30 and the electrolyte channel portion which is more remote from the third channel port, in this case, the upstream channel portion, as illustrated in FIG. 7B. The AC voltage applied is typically in the range 1 kHz to 1 MHz, preferably about 10 kHz, and having an electric field strength in the range 500–2000 V/cm, typically about 1,000 V/cm. As shown in FIG. 7B, the alternating voltage field is effective to produce dielectric focusing of sample components at two regions within the channel network. The first region, indicated at 112, is at or just upstream of the upstream end of sample volume 110. Because of the proximity of this region to the sample volume, sample components are able to concentrate in this region and sample material is moved past the elbow formed by the first channel and the electrolyte channel. Thus, the concentration of sample components can be controlled, within limits, by the duration of the sample-loading step.

The second region of dielectric focusing (not shown) is near the elbow of the third side channel and the electrolyte channel. This region is sufficiently remote from the sample volume that sample components therein are unable to concentrate in this region, and so only electrolyte components are present in this region. The net result of the sample loading, as indicated in FIG. 7B, is the formation of a small region 112 of highly concentrated sample components, and a downstream volume of much less concentrated components. It will be appreciated that for optimal sample loading, the sample supplied from reservoir is relatively dilute, and the sample-loading period is log-enough to produce a highly concentrated sample mixture.

In the sample-injection step, a DC voltage is applied across the upstream and downstream portions of the electrolyte channel to move the concentrated sample region and downstream sample volume into and through the electrolyte channel, as shown in FIG. 7C. During this migration, a DC voltage potential is also applied to the first and second side channels, to push back sample material in the two channels from the electrolyte channel, to reduce sample contamination from the side channels, as described above. Since the third channel does not contain sample material, the voltage of this channel is allowed to float, also to prevent unwanted movement of the sample into this channel.

Another embodiment of this method can be illustrated with respect to the side-channel configuration shown in FIG. 3, where the sample side channel is axially aligned or nearly so with one of the other side channels. With reference to the elements identified in FIG. 3, sample material is initially injected from first side channel 76 through a segment of the electrolyte channel into second side channel 80, by applying a DC voltage across the two channels, to produce a sample volume between the two channels. At the same time, an AC voltage is applied across the upstream reservoir ("B) and third channel 78 (which is axially aligned with the first channel), to produce a single region of dielectric focusing near the junction of the aligned side channels and the electrolyte channel. With this simultaneous application of DC and AC voltages across the three side channels and upstream channel portion, sample material accumulates and concentrates by dielectric focusing at the upstream end of the sample volume. The volume is then injected, as above, to carry the volume with its concentrated sample region into the downstream portion of the electrolyte channel.

The sample-concentration method provides significant advantages over dielectric focusing methods proposed in the prior art. In particular, by providing a third, remote side channel that is not involved in sample movement, dielectric sample-component focusing can occur at a selected region adjacent the sample volume and at a position remote from the sample volume, allowing sample concentration at one region only.

From the foregoing, it will be appreciated how various objects and features of the invention are met. The methods employing the subject devices may be associated with the transfer to the microstructures of the devices of volumes ranging from about 1 nl to 500 $\mu$l, with volumes ranging from about 10 nl to 0.5 ml, usually 20 nl to 0.1 ml. The volumes may be transferred by any efficient means, including pins, ink-jet dispensers, other piezoelectric devices, pipettes, etc.

The subject injectors may be used to provide predetermined volumes for numerous purposes. The defined plugs may be used in genomics, using the plug for identification of DNA sequences, for DNA sequencing, for detection of single nucleotide polymorphisms ("snps"), where a variety of tags for identifying particular snps may be involved, or other DNA analyses; for assays, particularly proteomics or immunoassays, including diagnostic assays, compound activity screening, compound reactivity, enzyme activity, and other analyses, identification of individual species, where the species can be detected, particularly in a mixture, where the components can be separated; and the like.

The subject injectors may be used to feed the sample to an electrophoretic separating channel, an HPLC, gas chromatograph, mass spectrometer or other device for identifying moieties. Various means can be used to connect the injector to the ancillary devices, such as capillary connectors and tubing. The subject invention provides for many advantages. A sharply defined sample as a predetermined volume plug can be produced, with some variation in size depending upon the cross-sectional area of the side channels, the electrode voltages and, in effect, potential gradients created at the junction region, the separation of the side channels, the cross-sectional area and shape of the main channel, etc. In this way, a device can be provided for reproducibly producing plugs that can be subjected to separations, allowing for sharply defined segments of the original plug. This allows for more sensitive accurate determinations of components of a sample in a reproducible manner, where plug volumes may vary from 1 nl to 50 nl or higher.

All publications and patent applications mentioned in this specification are indicative of the level of skill of those skilled in the art to which this invention pertains. All publications and patent applications set forth herein are incorporated by reference to the same extent as if each individual publication or patent application was specifically and individually indicated to be incorporate by reference.

The invention now having been fully described, it will be apparent to one of ordinary skill in the art that many changes and modifications can be made thereto without departing from the spirit or scope of the appended claims.

What is claimed is:

1. A method of injecting a liquid sample into an electrolyte channel in a microfluidics device having a channel network that includes an electrolyte channel having upstream and downstream channel portions and first, second, and third side channels that intersect the electrolyte channel between the two channel portions at first, second, and third ports, respectively, where at least one of the ports is axially spaced along the electrolyte channel from the other two ports, said method comprising
   (a) supplying a sample to the first side channel,
   (b) applying across the first side channel and at least one of the other two side channels, a voltage potential effective to move sample in the first channel into a volume element of the electrolyte channel extending between the first port and at least one other port which is axially offset from the first port,
   (c) simultaneously controlling the voltage applied to the three side channels, and optionally, at least one of said upstream and downstream channel end portions, to create a sample volume element in the electrolyte channel that has a desired leading- and trailing-edge shape and/or distribution of sample components within the volume element, and (d) simultaneously controlling the voltage applied to the upstream and downstream channel portion, and to at least two of the side channels, to advance the sample element having a desired leading- and trailing-edge shape and/or distribution of sample components in a downstream direction within the electrolyte channel.

2. The method of claim 1, for use in injecting a sample containing a plurality of sample components in a volume element of the sample components, wherein:

the first port is axially disposed between the second and third ports, applying step (b) is effective to move sample in the first channel into a volume element of the electrolyte chamber extending between the second and third ports, and controlling step (c) is effective to move an electrolyte solution from the upstream channel portion through the second port and an electrolyte solution from the downstream portion through the third port, thus to sharpen the upstream and downstream boundaries of the sample volume.

3. The method of claim 1, wherein the first port is axially aligned with the second port.

4. The method of claim 2, wherein the first port is axially spaced from the second and third ports.

5. The method of claim 2, wherein controlling step (d) is effective to move an electrolyte solution in the upstream channel portion successively through the second, first and third ports, to move sample contained in the three side channels away from the electrolyte channel.

6. The method of claim 1, for use in injecting a sample containing a plurality of sample components in a volume element, and prestacking the sample components within the volume element according to their electrophoretic mobilities, wherein:

the sample contains a plurality of components with different electrophoretic mobilities and one of a leading-edge ion having an electrophoretic mobility greater than that of said sample components or a trailing-edge ion having an electrophoretic mobility less than that of said sample components, the first port is axially disposed between the second and third ports, applying step (b) is effective to move sample in the first channel into a volume element of the electrolyte chamber extending between the second and third ports, controlling step (c) is effective to move an electrolyte solution from the upstream channel portion through the second port and an electrolyte solution from the downstream portion through the third port, thus to sharpen the upstream and downstream boundaries of the sample volume, where the electrolyte solution in both the upstream and downstream portions includes the other of the leading-edge or trailing-edge ion, and controlling step (d) is initially effective in stacking the sample components in the sample volume in accordance with their electrophoretic mobilities, by isotachophoretic separation.

7. The method of claim 6, wherein controlling step (d) is effective to move an electrolyte solution in the upstream channel portion successively through the second, first and third ports, to move sample contained in the three side channels away from the electrolyte channel.

8. The method of claim 1, for use in injecting a sample containing a plurality of sample components in a volume element, and prestacking the sample components within the volume element according to their electrophoretic mobilities, wherein:

the sample contains a plurality of components with different electrophoretic mobilities, the second port is axially disposed between the first and third ports, applying step (b) is effective to move sample in the first channel into a volume element of the electrolyte chamber extending between the first and second ports, controlling step (c) is effective to move a solution containing one of a leading-edge ion having an electrophoretic mobility greater than that of said sample components or a trailing-edge ion having an electrophoretic mobility less than that of said sample components from the third channel into the second channel, and controlling step (d) is initially effective in stacking the sample components in the sample volume in accordance with their electrophoretic mobilities, by isotachophoretic separation.

9. The method of claim 8, wherein controlling step (d) is effective to move an electrolyte solution in the upstream channel portion successively through the second, first and third ports, to move sample contained in the side channels away from the electrolyte channel.

10. The method of claim 1, for use in injecting a sample containing one or more sample components, and concentrating the component(s) at the upstream or downstream side of the sample volume, wherein:

the first, second, and third ports are axially spaced from one another, and the second port is disposed between the first and third ports, applying step (b) includes applying a DC voltage potential across the first and second side channels, to move sample in the first channel into a volume element of the electrolyte chamber extending between the first and second ports, and controlling step (c) includes applying an AC voltage between the third side channel and an upstream or downstream channel portion, to form a dielectric focusing field adjacent the upstream or downstream end of the sample plug effective to concentrate sample components in the sample volume at an end of the sample volume adjacent the channel portion to which the AC voltage is applied.

11. The method of claim 10, wherein the first, second, and third ports are positioned along the electrolyte channel in an upstream-to-downstream direction, and controlling step (c) includes applying an AC voltage between the upstream channel portion and the third side channel.

12. The method of claim 10, wherein the first and third channels are axially aligned or nearly so on opposite sides of the electrolyte channel, the second channel is axially spaced from the first and third channels, and controlling step (c) includes applying an AC voltage between the third channel and the adjacent upstream or downstream channel end portion.

13. A microfluidic system designed for use in injecting a defined-volume liquid sample into an electrolyte channel, for transport through the channel, comprising a microfluidic device having a channel network that includes such an electrolyte channel having upstream and downstream channel portions and first, second, and third side channels that intersect the electrolyte channel between the two channel portions at first, second, and third ports, respectively, where at least one of the ports is axially spaced along the electrolyte channel from the other two ports, ports for supplying liquid medium to the electrolyte channel and the side channels, upstream and downstream electrodes, and first, second, and third electrodes adapted to communicate with liquid medium contained in upstream and downstream portions of the electrolyte channel, and the first, second, and third side channels, respectively, and a voltage controller operatively connected to the upstream downstream, and first, second, and third electrodes, which operates to (a) applying across the first side channel and at least one of the other two side channels, a voltage potential effective to move a liquid sample contained in the first channel into a volume element of the electrolyte chamber extending between the first and at least one other port which is axially offset from the first port, (b) simultaneously control the voltage applied to the three side channels, and at least one of said upstream and downstream channel end portions, to create a sample volume element in the electrolyte channel that has a desired leading- and trailing-edge shape and/or distribution of sample components within the volume elements, and (c) simultaneously control the voltage applied to the upstream and downstream channel portion, and to at least two of the side channels, to advance the sample element having a desired leading- and trailing-edge shape and/or distribution of sample components in a downstream direction within the electrolyte channel.

14. The system of claim 13, for use in injecting a sample containing a plurality of sample components in a volume element of sample components, wherein:

the first port is axially disposed between the second and third ports, applying step (b) is effective to move sample in the first channel into a volume element of the electrolyte chamber extending between the second and third ports, and controlling step (c) is effective to move an electrolyte solution from the upstream channel portion through the second port and an electrolyte solution from the downstream portion through the third port, thus to sharpen the upstream and downstream boundaries of the sample volume.

15. The system of 14, wherein controlling step (d) is effective to move an electrolyte solution in the upstream channel portion successively through the second, first and third ports, to move sample contained in the three side channels away from the electrolyte channel.

16. The system of claim 13, for use in injecting a sample containing a plurality of sample components in a volume element, and prestacking the sample components within the volume element according to their electrophoretic mobilities, where the sample contains a plurality of components with different electrophoretic mobilities and a leading-edge ion having an electrophoretic mobility greater than that of said sample components, wherein the first port is axially disposed between the second and third ports, applying step (b) is effective to move sample in the first channel into a volume element of the electrolyte chamber extending between the second and third ports, controlling step (c) is effective to move an electrolyte solution from the upstream channel portion through the second port and an electrolyte solution from the downstream portion through the third port, thus to sharpen the upstream and downstream boundaries of the sample volume, where the electrolyte solution in both the upstream and downstream portions includes a trailing-edge ion having an electrophoretic mobility less than that of said sample components, and controlling step (d) is initially effective in stacking the sample components in the sample volume in accordance with their electrophoretic mobilities, by isotachophoretic separation.

17. The system of claim 13, for use in injecting a sample containing a plurality of sample components in a volume element, and prestacking the sample components within the volume element according to their electrophoretic mobilities, where the sample contains a plurality of components with different electrophoretic mobilities and a leading-edge ion having an electrophoretic mobility greater than that of said sample components, wherein:

the second port is axially disposed between the first and third ports, applying step (b) is effective to move sample in the first channel into a volume element of the electrolyte chamber extending between the first and second ports, controlling step (c) is effective to move a solution containing one of a leading-edge ion having an electrophoretic mobility greater than that of said sample components or a trailing-edge ion having an electrophoretic mobility less than that of said sample components from the third channel into the second channel, and controlling step (d) is initially effective in stacking the sample components in the sample volume in accordance with their electrophoretic mobilities, by isotachophoretic separation.

18. The system of claim 13, for use in injecting a sample containing one or more sample components, and concentrating the component(s) at the upstream or downstream side of the sample volume, wherein:

the first, second, and third ports are axially spaced from one another, and the second port is disposed between the first and third ports, applying step (b) includes applying a DC voltage potential across the first and second side channels, to move sample in the first channel into a volume element of the electrolyte chamber extending between the first and second ports, and controlling step (c) includes applying an AC voltage between the third side channel and an upstream or downstream channel portion, where the first and second ports are disposed between and spaced from the third side channel and channel portion to which the AC voltage is applied, thereby to concentrate sample components in the sample volume at an end of the sample volume adjacent the channel portion to which the AC voltage is applied.

19. The system of claim 13, for use in injecting a sample containing one or more sample components, and concentrating the component(s) at the upstream or downstream side of the sample volume, wherein:

the first and third channels are axially aligned or nearly so on opposite sides of the electrolyte channel, the second channel is axially spaced from the first and third channels applying step (b) includes applying a DC voltage potential across the first and second side channels, to move sample in the first channel into a volume element of the electrolyte chamber extending between the first and second ports, and controlling step (c) includes applying an AC voltage between the third channel and the adjacent upstream or downstream channel end portion between the third side channel and an upstream or downstream channel portion, thereby to concentrate sample components in the sample volume at an end of the sample volume adjacent the channel portion to which the AC voltage is applied.

* * * * *